(12) United States Patent
Overes

(10) Patent No.: US 8,460,294 B2
(45) Date of Patent: Jun. 11, 2013

(54) INTRAMEDULLARY NAIL

(75) Inventor: Tom Overes, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 119 days.

(21) Appl. No.: 13/098,935

(22) Filed: May 2, 2011

(65) Prior Publication Data
US 2012/0109127 A1 May 3, 2012

Related U.S. Application Data

(60) Provisional application No. 61/362,937, filed on Jul. 9, 2010.

(51) Int. Cl.
*A61B 17/72* (2006.01)

(52) U.S. Cl.
USPC .............................................. 606/62; 606/66

(58) Field of Classification Search
USPC ...................................................... 606/62–68
See application file for complete search history.

(56) References Cited

U.S. PATENT DOCUMENTS

| | | | |
|---|---|---|---|
| 4,502,160 A | 3/1985 | Moore et al. | |
| 4,541,424 A | 9/1985 | Grosse et al. | |
| 4,976,713 A | 12/1990 | Landanger et al. | |
| 5,505,734 A * | 4/1996 | Caniggia et al. | 606/63 |
| 6,106,528 A | 8/2000 | Durham et al. | |
| 6,221,074 B1 * | 4/2001 | Cole et al. | 606/62 |
| 6,228,086 B1 | 5/2001 | Wahl et al. | |
| 6,296,645 B1 | 10/2001 | Hover et al. | |
| 6,491,696 B1 * | 12/2002 | Kunkel | 606/105 |
| 6,569,165 B2 | 5/2003 | Wahl et al. | |
| 6,709,436 B1 | 3/2004 | Hover et al. | |
| 6,783,529 B2 | 8/2004 | Hover et al. | |
| 6,786,908 B2 | 9/2004 | Hover et al. | |
| 6,808,527 B2 | 10/2004 | Lower et al. | |
| 6,921,400 B2 | 7/2005 | Sohngen | |
| 6,926,719 B2 | 8/2005 | Sohngen et al. | |
| 6,932,819 B2 | 8/2005 | Wahl et al. | |
| 7,081,119 B2 * | 7/2006 | Stihl | 606/96 |
| 7,311,710 B2 | 12/2007 | Zander | |
| 7,608,075 B2 | 10/2009 | Tornier | |

(Continued)

FOREIGN PATENT DOCUMENTS

| | | |
|---|---|---|
| CN | 2394586 | 9/2000 |
| CN | 2502656 | 7/2002 |

(Continued)

*Primary Examiner* — Jan Christopher Merene
(74) *Attorney, Agent, or Firm* — Woodcock Washburn LLP

(57) ABSTRACT

An intramedullary device includes an intramedullary nail extending along a longitudinal axis from a proximal end to a distal end, a proximal portion of the intramedullary nail including a cavity extending from an opening at the proximal end along the longitudinal axis and a locking hole extending transversely therethrough along with a first insert sized and shaped for insertion into the cavity along the longitudinal axis thereof and including a transverse bore aligning with the locking hole and a second insert for engaging an inner surface of the cavity proximally of the first insert to retain the first insert within the cavity and including a central bore extending longitudinally therethrough for coupling to an insertion instrument.

21 Claims, 3 Drawing Sheets

U.S. PATENT DOCUMENTS

| | | | |
|---|---|---|---|
| 7,763,021 B2 | 7/2010 | Cole et al. | |
| 8,066,706 B2 * | 11/2011 | Schlienger et al. | 606/64 |
| 8,298,234 B2 * | 10/2012 | Ferrante et al. | 606/64 |
| 2003/0114855 A1 * | 6/2003 | Wahl et al. | 606/67 |
| 2003/0195515 A1 * | 10/2003 | Sohngen | 606/62 |
| 2006/0111717 A1 | 5/2006 | Saueressig et al. | |
| 2007/0100343 A1 * | 5/2007 | Cole et al. | 606/67 |
| 2008/0039857 A1 | 2/2008 | Giersch et al. | |
| 2008/0058829 A1 | 3/2008 | Buscher et al. | |
| 2008/0183171 A1 * | 7/2008 | Elghazaly et al. | 606/64 |
| 2008/0262496 A1 | 10/2008 | Schlienger et al. | |
| 2008/0294164 A1 | 11/2008 | Frank et al. | |
| 2009/0048600 A1 | 2/2009 | Matityahu et al. | |
| 2009/0306718 A1 | 12/2009 | Tipirneni et al. | |
| 2010/0094293 A1 | 4/2010 | McClellan et al. | |
| 2010/0152740 A1 | 6/2010 | O'Reilly et al. | |
| 2010/0191240 A1 | 7/2010 | Prager et al. | |

FOREIGN PATENT DOCUMENTS

| | | |
|---|---|---|
| CN | 2624839 | 7/2004 |
| CN | 2676850 | 2/2005 |
| CN | 2812857 | 9/2006 |
| CN | 2922822 | 7/2007 |
| DE | 3245680 | 10/1983 |
| DE | 3413596 | 11/1985 |
| DE | 4240277 | 6/1993 |
| DE | 10110246 | 10/2002 |
| EP | 0306709 | 8/1987 |
| EP | 0951873 | 10/1999 |
| EP | 1099413 | 5/2001 |
| EP | 1415599 | 5/2004 |
| WO | 98/41161 | 9/1998 |
| WO | 2004/100810 | 11/2004 |

* cited by examiner

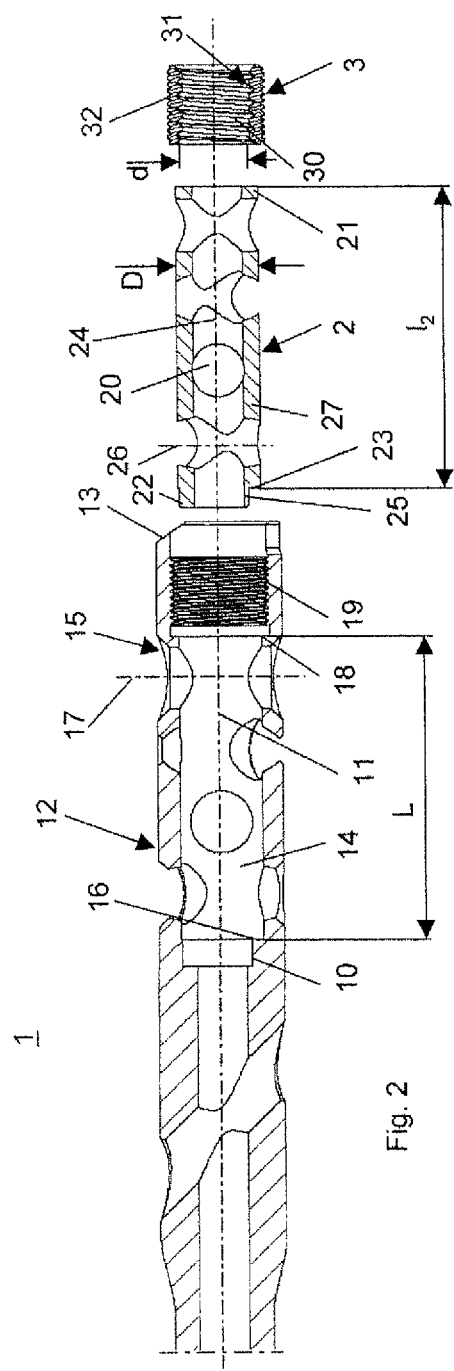
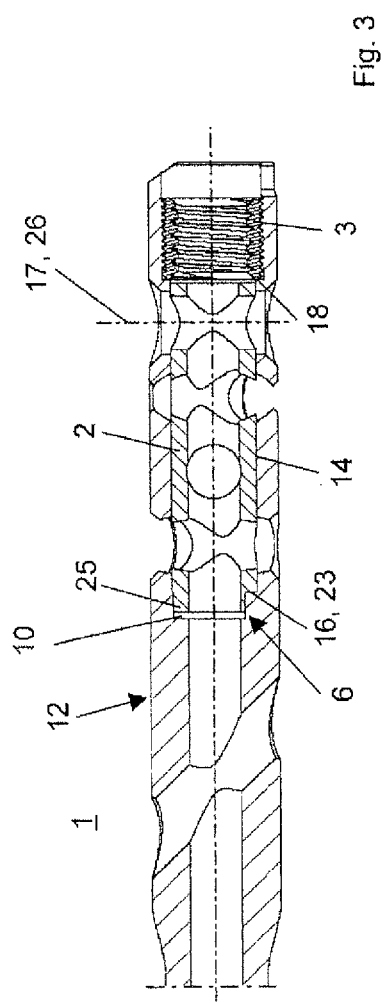
Fig. 2
Fig. 3

INTRAMEDULLARY NAIL

PRIORITY CLAIM

The present application claims priority to U.S. Provisional Application Ser. No. 61/362,937 filed on Jul. 9, 2010 and entitled "Intramedullary Nail," the entire disclosure of which is incorporated herein by reference.

FIELD OF THE INVENTION

The present invention generally relates to an intramedullary nail for fixation of fractured bones and more particularly to an intramedullary nail comprising an attachment structure for an insertion instrument and an insert for firmly securing locking screws to the intramedullary nail.

BACKGROUND

Intramedullary nails are commonly used as bone fixation devices for osteosynthesis purposes. Often these intramedullary nails feature locking screws inserted transversely through the intramedullary nail for either stabilizing the intramedullary nail in the bone or for fixation of individual bone fragments. These intramedullary nails may permit multiple locking screws to be inserted therethrough at different angles relative to one another. The locking screws are often secured in the intramedullary nail via a plastic bushing or ring preventing the screw from migrating out of the intramedullary nail due to micro-motion or other loads. To secure these screws in the intramedullary nail, an interference fit and a forced tapping of the screw into the bushing is generally applied. Other fixation features include metal interfaces that may be mechanically deformed and/or permit forced tapping in metal. These bushings should be formed of a material that is biocompatible. However, there is limited availability of such a material. One such available plastic material is Ultra High Molecular Weight Poly-Ethylene (UHMWPE), which is a material that has been approved worldwide for implantation. Although the biocompatibility of this material is ideal, the material is difficult to process with required accuracy using conventional processing and molding techniques.

An example of a locking intramedullary nail including transverse locking holes and an insert for securing the locking screws in these locking holes is known from EP Patent No. B 0 306 709 DAUERER. This known intramedullary nail comprises a proximal and a distal insert with transverse bores having a diameter smaller than the outer diameter of the locking screws so as to secure the locking screws in the locking holes of the intramedullary nail. The insert is slidably inserted into the central cavity of the intramedullary nail. This known intramedullary nail, however, does not comprise an attachment structure at the proximal end to fix an insertion instrument to the nail.

One problem associated with the above described intramedullary nails involves the attachment mechanism for an insertion handle or aiming device which is usually arranged at the proximal end of commonly used intramedullary nails is that the insert must have a small outer diameter in order to be introduced through a central opening of the attachment mechanism.

Thus, there remains a need for an improved intramedullary nail for a rigid fixation between the nail and the bone including an attachment mechanism for a surgical instrument and an insert, which permits the locking screws to be firmly secured in the locking holes of the intramedullary nail.

SUMMARY OF THE INVENTION

The present invention relates to an intramedullary nail having an attachment mechanism for an insertion instrument and an insert with transverse holes that are adapted and configured to firmly secure locking screws in the intramedullary nail.

According to the present invention, an intramedullary nail is extending along a longitudinal axis from a proximal end to a distal end, the nail comprising a cavity extending from an opening at the proximal end along the longitudinal axis and a first locking hole extending transversely through the nail sized and shaped to receive a locking screw therethrough along with a first insert sized and shaped for insertion into the cavity including a first transverse bore arranged so that, when the insert is in the desired position within the cavity, the first bore is aligned with the first locking hole so that a locking screw inserted through the first locking hole passes through the insert via the first bore and a second insert sized and shaped to be lockingly received within the cavity proximal of the insert to lock the insert at the desired position in the cavity.

Some advantages of the intramedullary nail according to the invention are that the insert does not have to be assembled through an attachment mechanism, e.g. an internal thread at the proximal end of the intramedullary nail and can therefore have an increased diameter. In addition, due to the increased diameter, the insert can be manufactured from Ultra High Molecular Weight Poly-Ethylene (UHMWPE) by using conventional processing and molding techniques. Further, due to the increased diameter of the insert, the locking screws can be firmly secured in the transverse bores of the insert and consequently in the locking holes of the intramedullary nail.

In one exemplary embodiment of the intramedullary nail, the first insert has an outer diameter D and the central bore has an inner diameter d and wherein the outer diameter D is greater than the inner diameter d of the central bore of the second insert.

In a further exemplary embodiment of the intramedullary nail, the first insert is made of Ultra High Molecular Weight Poly-Ethylene (UHMWPE). Preferably, the second insert and the intramedullary nail are made of TAN.

In another exemplary embodiment of the intramedullary nail, the first insert has an anti-rotation mechanism for preventing rotation of the first insert in the cavity in the intramedullary nail. Due to the anti-rotation mechanism the first insert is kept in a rotatively fixed position relative to the intramedullary nail so that the transverse bores in the first insert are aligned with the locking holes in the proximal part of the intramedullary nail.

In again another exemplary embodiment of the intramedullary nail, the first insert has more than one transverse bore.

In yet a further exemplary embodiment of the intramedullary nail, at least two transverse bores in the first insert extend in different directions.

In still a further exemplary embodiment of the intramedullary nail the second insert is fixed in the cavity of the intramedullary nail by one or more laser-welds. Preferably, the laser weld is a circumferential weld. Alternatively, the laser-welds are two small longitudinal laser-welds. Additionally, the second insert can be fixed in the cavity in the intramedullary nail via an external thread or a press-fit.

In another exemplary embodiment, the first insert has a cylindrical shape.

According to a further aspect of the present invention, an assembly is provided comprising an intramedullary nail and one or more locking screws, wherein the locking screws have a greater diameter than the transverse bores in the first insert.

In accordance with another aspect of the present invention, a method for assembling the intramedullary nail according to the invention is provided which comprises the steps of inserting a first insert into a cavity of a intramedullary nail, the intramedullary extending along a longitudinal axis from a proximal end to a distal end and including a first locking hole extending transversely through the nail sized and shaped to receive a locking screw therethrough, the cavity extending from an opening at the proximal end along the longitudinal axis, the insert including a first transverse bore arranged so that, when the insert is in the desired position within the cavity, the first bore is aligned with the first locking and inserting a second insert into the cavity of the intramedullary nail, the second insert sized and shaped to be lockingly received within the cavity proximal of the insert to lock the insert at the desired position in the cavity.

BRIEF DESCRIPTION OF THE DRAWINGS

A preferred embodiment of the present invention will be described in the following by way of example and with reference to the accompanying drawings in which:

FIG. 2 illustrates an exploded view in a longitudinal section of the embodiment of the intramedullary nail of FIG. 1;

FIG. 3 illustrates a longitudinal section of the embodiment of the intramedullary nail of FIG. 1 in the assembled state;

DETAILED DESCRIPTION

Figure 1:
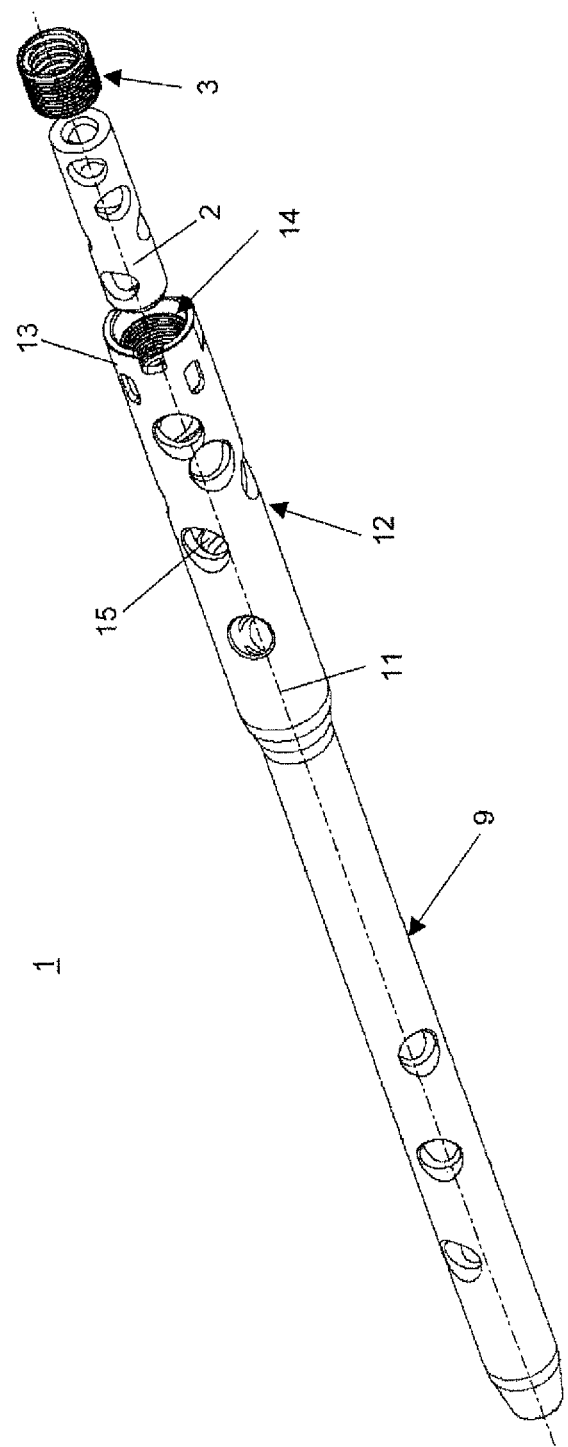
FIG. 1 illustrates a perspective exploded view of an exemplary embodiment of the intramedullary nail according to the present invention.

The present invention may be further understood with reference to the following description and the appended drawings, wherein like elements are referred to with the same reference numerals. The present invention generally relates to an intramedullary nail for fixation of fractured bones and more particularly to an intramedullary nail comprising an attachment structure for an insertion instrument and an insert for firmly securing locking screws to the intramedullary nail. It should be noted that the terms "proximal" and "distal" as used herein are intended to refer to a direction toward (proximal) and away from (distal) a user of the intramedullary nail.

As shown in FIGS. 1 to 5, an intramedullary nail 1 extends along a longitudinal axis 11 from a proximal end 13 to a distal end and includes a cavity 14 extending through a proximal portion 12 thereof. The intramedullary nail 1 further comprises a first insert 2 and a second insert 3 insertable through the cavity 14. The intramedullary nail 1 includes the proximal portion 12 and a distal portion 9, the proximal portion 12 including the cavity 14 extending longitudinally therethrough and a plurality of locking holes 15 for receiving locking screws extending transversely therethrough. The first insert 2 is inserted into the cavity 14 and the second insert 3 is inserted into the cavity 14 proximally of the first insert 2. The cavity 14 extends coaxially with the longitudinal axis 11 and is open at the proximal end 13. The cavity 14 may include an enlarged diameter portion at the proximal end 13 including an internal thread 19 extending thereabout for engaging the second insert 3. Further, the cavity 14 may also include a contraction which forms an axial stop 16 to prevent the first insert 2 from moving distally therepast toward the distal part 9 of the intramedullary nail 1. The plurality of locking holes 15 extend through the proximal portion 12 of the intramedullary nail 1 transversely to the longitudinal axis 11. Each of the locking holes 15 have a hole axis 17 and are arranged in such a manner that the hole axis 17 of each of the locking holes 15 orthogonally cuts the longitudinal axis 11 of the intramedullary nail 1. Further, the locking holes 15 are spaced apart from each other along the longitudinal axis 11 of the intramedullary nail 1. The locking holes 15 are staggeredly arranged so that the hole axes 17 of the four locking holes 15 extend at an angle relative to one other when viewed in a cross-section orthogonal to the longitudinal axis 11 of the intramedullary nail 1. In a preferred embodiment, the intramedullary nail 1 includes four locking holes 15. It will be understood by those of skill in the art, however, that the intramedullary nail 1 may include any number of locking holes 15.

The first insert 2 may have a cylindrical body 27 extending along a central axis 24 from a proximal end 21 to a distal end 22. The first insert 2 includes an eccentric nose 25 at the distal end 22. The first insert 2 is coaxially positioned in the cavity 14 and includes a plurality of transverse bores 20 extending transversely therethrough, each of the transverse bores 20 having a bore axis 26. The transverse bores 20 are arranged in such a manner that the bore axes 26 extend orthogonally of the central axis 24 and are equally spaced apart and extend at equal angles relative to each other, corresponding to a position of the locking holes 15 in the proximal part 12 of the intramedullary nail 1. Thus, when inserted into the cavity 14, the transverse bores 20 in the first insert 2 may be exactly aligned with the locking holes 15 in the proximal part 12 of the intramedullary nail 1.

As illustrated in FIG. 3, the eccentric nose 25 engages a complementarily shaped eccentric portion 10 in the cavity 14 when the first insert 2 is inserted in the cavity 14. Thus, the eccentric nose 25 and the eccentric portion 10 form an anti-rotation mechanism 6, which prevents the first insert 2 from rotating relative to the cavity 14 in the intramedullary nail 1. The cylindrical body 27 of the first insert 2 may also include a stop face 23 proximally of the eccentric nose 25 for contacting the axial stop 16 in the cavity 14 of the intramedullary nail 1 when the first insert 2 is completely inserted in the cavity 14. The second insert 3 may also be cylindrical, including a central bore 30. The second insert 3 is fixedly positioned in the cavity 14 coaxially and proximally of the first insert 2. The second insert 3 may have an internal thread 31 along an inner surface of the central bore 30 and an external thread 32 along an outer surface thereof, which corresponds to the internal thread 19 of the enlarged diameter portion of the cavity 14 such that the second insert 3 may threadedly engage the cavity 14. The cavity 14 also includes a shoulder 18 therein, which is distal of the enlarged portion so that the second insert 3 contacts the shoulder 18 and is prevented from moving distally therepast, further into the cavity 14.

The first insert 2 has been described as having an eccentric nose 25. It will be understood by those of skill in the art, however, that other nose configurations are also possible. For example, the nose could be concentric but have a flattened edge to provide the anti-rotation mechanism with a complementarily shaped eccentric portion in a cavity. In another example, the nose could feature two or more complementary edges that have rotational symmetry of, for example, order 2.

As illustrated in FIG. 2, a portion of the cavity 14 which receives the first insert 2 and which is axially limited by the axial stop 16 and by the shoulder 18 has a length L which is slightly greater than a length $l_2$ of the cylindrical body 27 of the first insert 2. The central bore 30 of the second insert 3 may act as a fixation structure for coupling an insertion instrument such as, for example, an insertion handle and/or an aiming device, to the intramedullary nail 1. The first insert 2 has an outer diameter D and the central bore 30 has an inner diameter d, wherein the outer diameter D of the insert 2 is greater than the inner diameter d of the central bore 30 of the second insert 3. Thus, once the first insert 2 is fully inserted in the cavity 14 it cannot be axially displaced upon insertion of the second insert 3 but is retained by the second insert 3 in the cavity 14.

Figure 4:
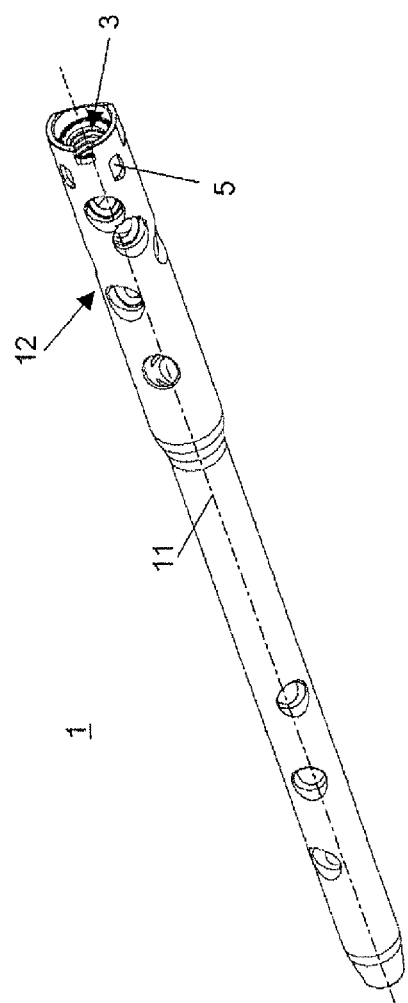
FIG. 4 illustrates a perspective view of the embodiment of the intramedullary nail of FIG. 1 in the assembled state.
Figure 5:
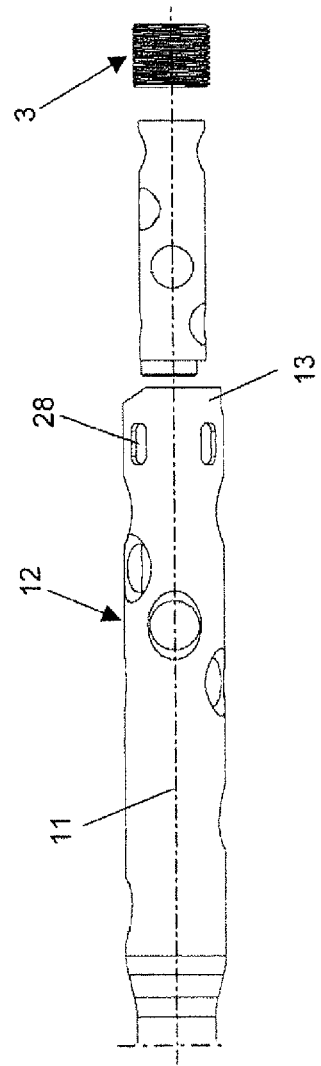
FIG. 5 illustrates a lateral exploded view of the embodiment of the intramedullary nail of FIG. 1.

As illustrated in FIGS. 4 and 5, the second insert 3 is fixed in the cavity 14 of the intramedullary nail 1 via a longitudinal laser-weld 5, which may be positioned in an oblong opening 28, which extends through a wall of the proximal portion 12 of the intramedullary nail 1. In one exemplary embodiment, the intramedullary nail 1 includes two longitudinal laser-welds 5 and two oblong openings 28 that are axially located between the shoulder 18 in the cavity 14 and the proximal end 13 of the intramedullary nail 1. Further, the two oblong openings 28 have a long axis each which extends parallel to the longitudinal axis 11 of the intramedullary nail 1 and when viewed in a cross-section orthogonal to the longitudinal axis 11 the two oblong openings 28 are arranged at an angle relative to one another. In another embodiment, the second insert 3 may be welded, for example circumferentially, to the cavity 14 at the proximal end 13 of the intramedullary nail 1, between an exterior surface of the second insert 3 and an interior of the enlarged diameter portion at the proximal end 13 which receives the second insert 3.

Furthermore, the transverse bores 20 in the first insert 2 have a smaller diameter than the locking screws (not shown) used to lock the intramedullary nail 1 in a bone. Therefore, the thread of the locking screw cuts into the wall which limits the respective transverse bore 20 so that the locking screws are secured against loosening within the transverse bores 20 and consequently within the locking holes 15 of the intramedullary nail 1 so that a rigid fixation of the locking screws in the intramedullary nail 1 can be achieved.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. An intramedullary nail defining a proximal end and a distal end spaced apart from the proximal end along a longitudinal axis, the intramedullary nail comprising:
   a shaft extending between the proximal and the distal ends, the shaft defining an opening at the proximal end, and a cavity that extends from the opening toward the nail distal end, the cavity having a proximal portion disposed at the proximal end, an eccentric portion that is distal to the proximal portion, and a distal portion that is distal to the eccentric portion, the eccentric portion of the cavity defining an eccentric portion center axis, the eccentric portion center axis being offset from the longitudinal axis;
   a locking hole extending transversely through the nail sized and shaped to receive an anchor therethrough;
   a first insert sized and shaped for insertion into the proximal and eccentric portions of the cavity, the first insert defining a first insert body extending between an insert proximal end and an insert distal end, a projection that protrudes distally from the insert distal end, the insert body having a circular cross-sectional dimension, the projection configured to be received by the eccentric portion of the cavity, and a transverse bore extending through the first insert body, wherein the first insert is configured such that the projection can be inserted into the eccentric portion of the cavity and the locking hole and the transverse bore are aligned,
   a second insert sized and shaped to be received within the cavity, the second insert extending between a second insert proximal end and a second insert distal end, the second insert configured such that when the second insert is inserted into the cavity, the second insert distal end is adjacent to the insert proximal end of the first insert.

2. The intramedullary nail according to claim 1, wherein the second insert includes a central bore having a coupling mechanism configured to receive an instrument to be coupled to the nail.

3. The intramedullary nail according to claim 2, wherein the first insert defines an outer cross-sectional dimension, and the central bore defines an inner cross-sectional dimension, wherein the outer cross-sectional dimension is larger than the inner cross-sectional dimension.

4. The intramedullary nail according to claim 1, wherein the first insert is formed of an Ultra High Molecular Weight Poly-Ethylene (UHMWPE) material.

5. The intramedullary nail according to claim 1, wherein the locking hole is first locking hole, wherein the intramedullary nail includes a second locking hole extending transversely through the nail.

6. The intramedullary nail according to claim 5, wherein the first and second locking holes extend through the nail at an angle relative to one another.

7. The intramedullary nail according to claim 5, wherein the first insert includes a second transverse bore, wherein when the insert is in the desired position in the cavity the second transverse bore is aligned with the second locking hole.

8. The intramedullary nail according to claim 1, wherein the second insert includes an external thread about an outer surface thereof, wherein the cavity defines an internal thread located at the proximal end of the shaft, wherein the external thread of the second insert is configured to engage the internal thread at a proximal end of the shaft.

9. The intramedullary nail according to claim 1, wherein the second insert is fixed in the cavity of the intramedullary nail by a laser-weld.

10. The intramedullary device according to claim 1, wherein the cavity includes a stop formed at the intersection of the proximal and eccentric portions, the stop configured to prevent the first insert from moving distally therepast.

11. The intramedullary nail according to claim 1, wherein the proximal portion of the cavity defines a first cross-sectional dimension and the eccentric portion of the cavity defines a second cross-sectional dimension that is less than the first cross-sectional dimension.

12. An intramedullary nail system, comprising:
an intramedullary nail extending along a longitudinal axis from a proximal end to a distal end, the nail comprising:
a shaft extending between the proximal and the distal ends, the shaft defining an opening at the proximal end, and a cavity that extends from the opening toward the nail distal end, the cavity having a proximal portion disposed at the proximal end, an eccentric portion that is distal to the proximal portion, and a distal portion that is distal to the eccentric portion, the eccentric portion of the cavity defining an eccentric portion center axis, the eccentric portion center axis being offset from the longitudinal axis;
a locking hole extending transversely through the nail;
a first insert sized and shaped for insertion into the proximal and eccentric portions of the cavity, the first insert defining a first insert body extending between an insert proximal end and an insert distal end, a projection that protrudes distally from the insert distal end, the insert body having a circular cross-sectional dimension, the projection configured to be received by the eccentric portion of the cavity, and a first transverse bore extending through the insert body, wherein the first insert is configured such that the projection can be inserted into the eccentric portion of the cavity and the locking hole and the transverse bore are aligned, and
a second insert sized and shaped to be received within the cavity, the second insert extending between a second insert proximal end and a second insert distal end, the second insert configured such that when the second insert is inserted into the cavity, the second insert distal end is adjacent to the insert proximal end of the first insert; and
an anchor sized and shaped to be inserted through the locking hole and the first transverse bore.

13. The intramedullary nail system according to claim 12, wherein the second insert includes a central bore having a coupling mechanism configured to lockingly receive an instrument to be coupled to the nail.

14. The intramedullary nail system according to claim 12, wherein the first insert is formed of an Ultra High Molecular Weight Poly-Ethylene (UHMWPE) material.

15. The intramedullary nail system according to claim 12, wherein the locking hole is a first locking hole, wherein the intramedullary nail includes a second locking hole extending transversely therethrough.

16. The intramedullary nail system according to claim 15, wherein the first and second locking holes extend therethrough at an angle relative to one another.

17. The intramedullary nail system according to claim 15, wherein the first insert includes a second transverse bore, wherein when the insert is in the desired position in the cavity, the second transverse bore is aligned with the second locking hole.

18. The intramedullary nail system according to claim 15, wherein the anchor is a first anchor, wherein the system further comprises a second anchor configured for insertion into the second locking hole and the second transverse bore.

19. The intramedullary nail system according to claim 12, wherein the proximal portion of the cavity defines a first cross-sectional dimension and the eccentric portion of the cavity defines a second cross-sectional dimension that is less than the first cross-sectional dimension.

20. A method for assembling an intramedullary nail, comprising:
inserting a first insert into desired position within a cavity of a intramedullary nail, the intramedullary extending along a longitudinal axis from a proximal end to a distal end, the nail defining an opening at the proximal end and including a locking hole, the cavity extending from the opening toward the nail distal end along the longitudinal axis, the cavity having a proximal portion disposed at the proximal end, an eccentric portion that is distal to the proximal portion, and a distal portion that is distal to the eccentric portion, the eccentric portion of the cavity defining an eccentric portion center axis, the eccentric portion center axis being offset from the longitudinal axis, wherein the first insert extends between an insert proximal end and an insert distal end, the first insert including a projection that extends distally from the insert distal end, the projection configured to be received by the eccentric portion of the cavity, and a transverse bore arranged so that, when the insert is in a desired position within the cavity, the projection is inserted into the eccentric portion of the shaft cavity, and the transverse bore is aligned with the locking hole; and
inserting a second insert into the cavity of the intramedullary nail, the second insert sized and shaped to be received within the cavity, the second insert extending between a second insert proximal end and a second insert distal end, the second insert configured such that when the second insert is inserted into the cavity, the second insert distal end is adjacent to the insert proximal end of the first insert.

21. The method of claim 20, further comprising fixing the second insert within the cavity via a laser-weld.

* * * * *